US00PP13417P3

(12) United States Plant Patent
Mukherjee et al.

(10) Patent No.: US PP13,417 P3
(45) Date of Patent: Dec. 24, 2002

(54) GLADIOLUS HYBRID PLANT 'BRICK BEAUTY'

(75) Inventors: Debashish Mukherjee, Himachal Pradesh (IN); Devendra Dhayani, Himachal Pradesh (IN); Jai Chand Rana, Himachal Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/812,959

(22) Filed: Mar. 27, 2001

(65) Prior Publication Data

US 2002/0144323 P1 Oct. 3, 2002

(51) Int. Cl.[7] ..... A01H 5/00

(52) U.S. Cl. ..... Plt./301

(58) Field of Search ..... Plt./301

*Primary Examiner*—Bruce R. Campell
*Assistant Examiner*—Annette Para
(74) *Attorney, Agent, or Firm*—Birch, Stewart, Kolasch & Birch, LLP

(57) ABSTRACT

The invention relates to a novel and distinct hybrid plant named 'Brick Beauty' (*Gladiolus sp.*) characterized by its attractive Brick red colored flowers with Dresden yellow color on the lip petals.

1 Drawing Sheet

FIELD OF THE INVENTION

Figure 1:
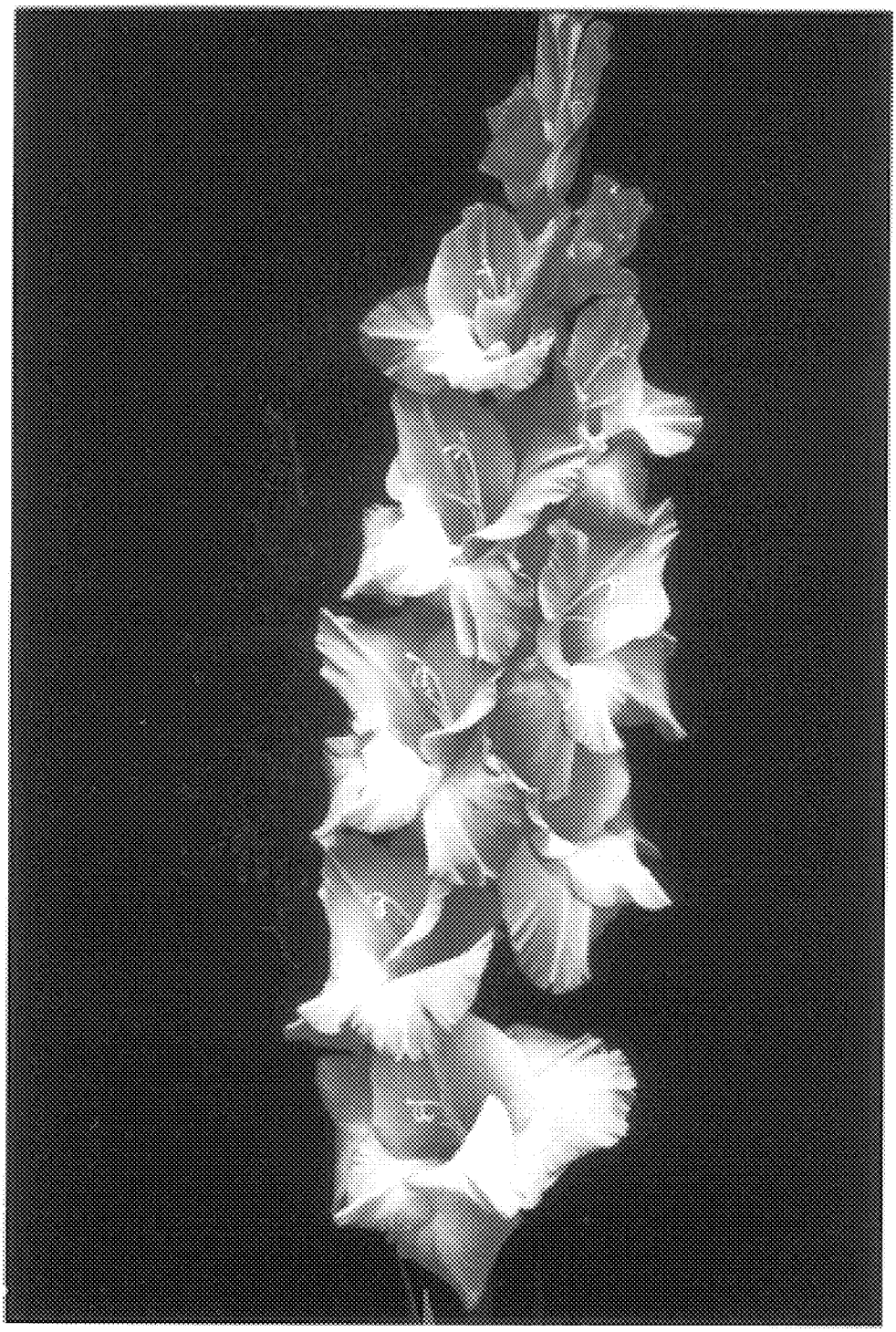

The present invention relates to a novel hybrid plant named 'Brick Beauty' and belonging to the family Iridaceae. The novel plant being a hybrid, has been developed in a breeding programme. The novel plant 'Brick Beauty' is propagated vegetatively by corms and hence can be maintained as a stable genotype. The plant of the invention is an ornamental plant widely cultivated for beautiful flowers which are of commercial and export value.

BACKGROUND OF THE INVENTION

Latin Name of the Genus of the Plant Claimed

The present invention relates to a new and distinct variety of gladiolus, a member of the Gladiolus genus.

Variety Denomination

The present invention relates to a new and distinct variety of gladiolus, a member of the Gladiolus genus. The novel plant is the hybrid between the gladiolus plants 'Vink Glory' and 'Eurovision', which are hybrid varieties.

Gladiolus is one of the important cut flowers throughout the world. The commercial cultivation is wide spread in temperate, tropical and subtropical climates. The demand of new varieties with better color, quality flowers, and planting materials is always existing in the floriculture trade.

The modern garden cultivators gladiolus come from diverse genetic parentages. It has cumulative heterozygosity for many characters inherent with complex genetic constitution. In gladiolus, diverse parents are crossed together and the cultivars and the species that differ widely in chromosome numbers are also cross-fertile. In the present invention, the desirable strains obtained in $F_1$ generation were perpetuated vegetatively without being segregated in the following generations, so that the cultivars which are available today may be $F_2$, $F_3$ to $F_8$ or so of a particular cross further blended with some extra parents at nearly every generation. Thus, they are not allowed to segregate freely in further generations because it is desirable to grow the plants asexually. Because of this reason, now the available modern cultivars have become so complex that the offspring obtained by crossing them, even two seedlings, do not appear similar [(Misra, 1975) Gladiolus Br. Assn. Newsletter, No.12, pp. 2–5].

The Applicants collected germplasm of different cultivars and hybrid varieties of gladiolus from National Botanical Research Institute Lucknow, India as per the list of gladiolus cultivars grown in India and described in the bulletin of 'gladiolus' Economic Botany Information Service by Sharma et al. published by the Director National Botanical Research Institute Lucknow, 1988. Germplasm of gladiolus was also collected from Netherlands in 1991 and various nurseries of Kalimpong, Darjeeling, West Bengal, India. The record of the collected germplasm of gladiolus was maintained in the accession register of the Floriculture Division of the Institute of Himalayan Bioresource Technology (IHBT), Palampur, India.

The Applicants initiated a breeding program to develop better types of gladiolus hybrids suitable to wide range of climatic conditions, and having wide range of characteristics such as better color, increased number of florets and spike length as per the international standards, better yield of corms and cormels, tolerant to the common diseases etc. The collected germplasm of gladiolus was planted in the experimental field of IHBT for their propagation and multiplication. In this breeding programme conventional breeding method (hybridization) was used. More than 100 cross combinations were made by using distinct varieties such as 'Oscar', 'Jester', 'Snow Princess', 'Eurovision', 'Ballerina', 'King Liar', 'Cherry Blossom', 'Her Majesty', 'Green Woodpecker', 'Friendship', 'Vink's Glory', 'Aldebaran', 'Red Beauty', 'Top Brass', 'Copper King', 'Bonfire', 'White Goddess', 'Sunny Boy', 'Tropic Sea' and 'Friendship Pink', etc.

Color description of some of the parentage as described in NAGC Bulletin.

'Oscar': Turkey red, throat blotched sulphur yellow.

'Green Woodpecker': Pea Green, throat blotched pea green spotted ruby red.

'Eurovision': Signal red, throat streaked pea green.

'Friendship Pink': Dawn Pink, throat blotched pea green having splashes ruby red.

'Aldebaran': Straw Yellow and throat blotched signal red.

As the aim is the production of seed of known parentage, emasculation in first three flowers in a selected spike is done before the opening of the flowers and stigma becomes receptive. Anthers are removed carefully from each flower. Emasculated flowers were covered with butter paper bags used for breeding purposes. Pollination was done in the emasculated flowers next day morning with in 24–30 hours with the pollens of the desired parents in the month of April–May 1991. The seeds were collected from mature pods in the month of August–September and were sown in beds under open field conditions and covered with dry grasses for moisture preservation in December 1991. The resultant seedlings were space planted in the field at Palampur in March–April 1992.

Many seedlings came out from a single cross combination. These plants were critically evaluated and tagged as per the desired color combinations, growth and flowering parameters. The corn and cormels of the selected hybrid plants were replanted continuously four years in the field for further evaluation and multiplications. Based on the superior performance for attractive color combination, compactness of flower spike, number of flowers per spike, length of flower spike, number of corm and cormels per plant evaluation and selection of superior quality hybrids were made.

Thus, the breeding program involved hybridization of commonly available gladiolus plants. In other words, the hybrids were developed by crossing parental genotypes involving sexual hybridization in the breeding programme.

The program yielded a number of hybrid plants out of which one genotype namely 'Brick Beauty' was selected and christened as 'Brick Beauty'. This plant was found to have new color, flower size, number of florets per spikes, length of flower spikes, better yield of corm and cormels and less prone to common diseases. Growing the plant on a commercial scale offers the horticulturists an improved and new variety, which can be commercially cultivated.

DETAILED DESCRIPTION OF THE INVENTION

Thus, the invention provides a new genotype christened as 'Brick Beauty'. This plant has been developed through planned breeding experiments conducted at Institute of Himalayan Resources, (IHBT) Palampur, Himachal Pradesh, India with defined aim to develop superior gladiolus genotypes. For this purpose, gladiolus varieties were collected from different sources and grown in the fields at Palampur, India for facilitating breeding program. The emasculation and pollination in different varieties were carried out during the months of April–May 1991. The seeds were collected in July–August 1991 and sown in beds under open field conditions and covered with dry grasses in December 1991. The resultant seedlings were space planted in the field at Palampur in March–April 1992. The corm and cormels of survived hybrid plants were replanted continuously four years for screening and multiplication.

Based on the superior performance for attractive color combination, compactness of flower spikes, number of flowers per spikes, length of flower spikes, number of flowers remains open at a time, number of corm and cormel production per plant, the plant of this invention ('Brick Beauty') was selected for further observation and evaluation.

Considering the superior characteristics like excellent color, number of flowers, compactness of flower spikes, plant height, ruffled-ness of flower petals, regeneration potential and freedom from common diseases, it was asexually reproduced through corms and cormels to maintain purity.

The selected hybrid 'Brick Beauty' was christened as 'Brick Beauty' and grown at row distance of 1 feet and plant to plant 6 inches for four consecutive years to study its growth and flowering performance and multiplication. Data were recorded on randomly selected twenty plants every year. The hybrid 'Brick Beauty' maintained uniformity in its growth and flowering performance.

EVIDENCE OF UNIFORMITY AND STABILITY

The hybrid 'Brick Beauty' has remained stable and uniform for its morphological characteristics and showed consistency in performance for various growth and flowering parameters during its evaluation and vegetative multiplication since 1992. Throughout the evaluation period of 'Brick Beauty', no variants were found from the normal population.

The genotype 'Brick Beauty' possesses standard type flowers of Brick red (RHS-35A) with Dresden yellow (RHS-5D) color on lip petals and the flower petals are ruffled which is quite clear from FIG. 1.

The genotype 'Brick Beauty' is distinct in regeneration potential.

BRIEF DESCRIPTION OF THE ACCOMPANYING PHOTOGRAPH

FIG. 1 is a photograph of field grown flower spike of IHBT-GH-190 ('Brick Beauty') depicting decorative type flowers of Brick red (RHS-35A) with Dresden yellow (RHS-5D) color on lip petals.

The plant of invention 'Brick Beauty' is thus a new and distinct hybrid plant, having the following combination of characters:

a) Color flowers are Brick red (RHS-35A) with Dresden yellow (RHS-2D) color on lip petals;

b) Ruffled petals.

c) Average days to flower: about 93 days.

d) Average number of flower spikes/plant is 1.93.

e) Average length of flower spikes is 115 cm.

f) Average number of flowers per spikes is 18.

OBJECTIVE DESCRIPTION OF THE GENOTYPE 'Brick Beauty'

The following is an objective description of the new variety.

1. Genus: Gladiolus.
2. Species: *Hybrid sp.*
3. Family: Iridacae.
4. Common name: Sward lily/gladiolus.
5. Average plant height: 134.61 cm.
6. Growth habit: Erect, uniform.

7. Average stem diameter: 1.12 cm.
8. Average number of leaves/plant: 7.24.
9. Average height of leaves: 52.03 cm.
10. Average days to flower: 93 days.
11. Type of flowers: Decorative.
12. Average number of spikes/plant: 1.93.
13. Average length of the flower spike: 115 cm.
14. Average number of flowers/spike: 18.0.
15. Flower color: Brick red (RHS-35A) with Dresden Yellow (RHS-2D) color on lip petals.
16. Type of petals: Petals ruffled.
17. Average number of flowers that remain open at a time: 8.86.
18. Average longevity of the 1$^{st}$ flower: 3.06 days.
19. Average diameter of 1$^{st}$ flower: 11.8 cm.
20. Average longevity of the spike: 9.59 days.
21. Average number of corms/plant: 1.98.
22. Average diameter of corms: 6.06 cm.
23. Average number of cormels/plant: 90.

The color specifications of the flower parts distinguishing 'Brick Beauty' from others within the same botanical and market class have been incorporated according to R.H.S. Color Chart published by The Royal Horticultural Society, 80 Vincent Square, London S W1P 2PE, 1995. The distinguishing characteristics are compared with other cultivars of same botanic and market class to emphasize the distinctiveness of 'Brick Beauty'.

The genotype IHBT-GH-190 ('Brick Beauty') was bred at the Institute of Himalayan Bioresource Technology (IHBT) under the programme of development of new varieties of gladiolus.

AGE AND GROWING CONDITIONS

The hybrid of the instant invention was raised in the year 1991 through the conventional method of breeding and the age of this hybrid is more than 10 years old. The hybrid was grown under open field conditions in the Palampur area of Himachal Pradesh. The altitude of Palampur is 1300 m above sea level (amsl) and thus, the environment is classified under a sub-humid, sub-temperature zone. The average maximum and minimum temperatures are 30° C. and 10° C., respectively. The average annual rainfall is 250 cm.

LEAVES

Leaves are cauline sheathed over lopped blades, sward shaped, linear-lanceolate. The base cuneate apex is acute or acuminate and both the ventral and the dorsal surface is moderate green (RHS—137C) with a smooth glabrous margin entire fibrous white venation parallel with prominent fibrous leaves 36.5–78.3 cm long from ground level (average—56.01 cm) with a width of 3.4–6.7 cm (average—4.72 cm).

PETALS (TEPALS)

Perianth, petaloid, actinomorphic tepals (perianth segments or petals) 6 are arranged in two whorl, 3 in each inner and outer whorl imbricate aestivation tepals sessile or short stalked (rarely). The shape and the size is variable. That is, 5–8.5 cm long 3.5–6.5 cm width oblong oblancolate base sub-cordate or cuneate. Apex obtuse or blunt margin entire oblique.

BUD SIZE AND COLOR

Buds are 5.58 cm to 8.02 cm long (bottom 3 buds were taken) and the average size 6.81 cm long. The diameter of the lower 3 buds ranging from 0.89 to 1.42 cm and the average is 1.24 cm. The color of the bud is nearest to (RHS—132 A).

REPRODUCTIVE ORGANS i) Androecium: Stamens 3 triandrous adnate to tepals shorter than tepals and stalk filaments white erect 3.0–3.5 cm long anther attached with the top of filament dithecous (bilobed) pale purple colored about 18 mm long extrose dorsifixed.

ii) Gynoecium: Ovary tricarpellary inferior triocular many ovules in each locule style single terminal longer than stamens pale white about 8 cm long stigma 3 lobed stalked flattened wavy villous 8–10 mm lobes narrow at the base with rounded apex.

Gladiolus plants are commercially propagated vegetatively through corms and cormels. The average diameter of the corm of 'Brick Beauty' is 6.06 cm. The number of cormels/plant is 90.

'Brick Beauty' is entirely different in color than its parents 'Vink's Glory' and 'Eurovision' and having Brick Red color (RHS—35 A) petals with Dresdan Yellow (RHS—5D) color on lip petals. Lip petals nicely ruffled. 'Vink's Glory' is light yellow color and 'Eurovision' is dark vermillion with white veins.

'Brick Beauty' is not a fragrant hybrid.

ASEXUAL REPRODUCTION METHOD

The hybrid seeds produced by the crossing of 'Vink's Glory' and 'Eurovision' were sown in the field. These seeds produced many different hybrid plants, which were screened based on their color and other growth and flowering parameters.

Seedling named 'Brick Beauty' produced one corm and 15 cormels in first year after harvesting. The corm and cormels were sown in field in the next growing season. The cormels became flowering size corms within a year. Again, in the next year, these corms and cormels were sown in the field to produce a large number of corms and cormels. This process was continued year after year for increasing the corm and cormel population.

Producing corm of gladiolus through cormels is asexual method of propagation for reproducing planting material.

We claim:

1. A novel and distinct gladiolus plant christened as 'Brick Beauty' characterized by the following combination of characteristics:

a) Color flowers are Brick red (RHS-35A) with Dresden yellow (RHS-2D) color on lips petals b) Ruffled petals c) Average days to flower: about 93 days d) Average number of flower spikes/plant is 1.93 e) Average length of flower spikes is 115 cm f) Average number of flowers per spikes is 18 and substantially as herein described and illustrated.

* * * * *